United States Patent [19]

Moessner

[11] Patent Number: 5,707,870
[45] Date of Patent: Jan. 13, 1998

[54] PROCESS FOR NEUTRALIZING ACIDS IN A SOLUTION OF SOLVENT AND POLYMER

[75] Inventor: Richard Crosby Moessner, Midlothian, Va.

[73] Assignee: E. I. Du Pont de Nemours and Company, Wilmington, Del.

[21] Appl. No.: 643,692

[22] Filed: May 6, 1996

Related U.S. Application Data

[63] Continuation-in-part of Ser. No. 299,379, Sep. 1, 1994, abandoned.

[51] Int. Cl.$^6$ .......................... G01N 35/08; G01N 33/44; G01N 31/00
[52] U.S. Cl. .................. 436/55; 436/61; 436/85; 436/100; 436/101; 436/163
[58] Field of Search ................. 436/55, 61, 85, 436/100, 101, 163

[56] References Cited

U.S. PATENT DOCUMENTS

| | | | |
|---|---|---|---|
| 3,287,324 | 11/1966 | Sweeny | 260/78 |
| 3,299,176 | 1/1967 | Longworth | 260/876 |
| 4,283,361 | 8/1981 | Longworth | 264/120 |
| 4,745,143 | 5/1988 | Mason et al. | 524/98 |
| 5,015,856 | 5/1991 | Gold | 250/339 |
| 5,097,130 | 3/1992 | Koashi et al. | 250/339 |
| 5,145,785 | 9/1992 | Maggard et al. | 436/8 |
| 5,192,509 | 3/1993 | Surjaatmadja et al. | 422/75 |
| 5,358,875 | 10/1994 | Goswami et al. | 436/124 |

OTHER PUBLICATIONS

Mattera, V.D., Jr. et al., Spectroscopic and thermal studies of ionic interactions, *Chemical Abstracts*, 105, No. 2, 30–31, Jul. 14, 1986.

Gallus–Olender, J., et al, Structural changes during the silica rubber filler precipitation investigated by IR and NIR spectroscopy, *Chemical Abstracts*, 99, No. 12, 62, Sep. 19, 1983.

Qaderi, S.B.A.; et al, Characterization of solutions and aqueous dispersions of epoxy/amidoamine resins, *Chemical Abstracts*, vol. 109, No. 6, 86, Aug. 8, 1988.

R.M. Silverstein et al, Spectrometric Identification of Organic Compounds, *John Wiley & Sons, Inc.*, Fourth Edition, 166–170; 1981.

Peter R. Hornsby, et al, The formation and properties of mineral–polyacid cements, *Journal of Materials Science*, 17, 3575–3592; 1982.

Kenji Tsunashima et al, Far–Infrared Study on the Zinc(II) Complex Salts of Ethylene–Methacrylic Acid Copolymer with 1,3–Bis(aminomethyl)cyclohexane, *Macromolecules*, American Chemical Society, 24, 5910–5913; 1991.

Y. Uemura, et al, Infrared Dichroism Studies of the Relaxation of Ethylene–Methacrylic Acid Copolymers and Their Salts, *Macromolecules*, 4, No. 4, 490–494; Jul.–Aug. 1971.

Yue Zhao, et al, Infrared Dichroic Study of Orientation Using Ionomers, *Macromolecules*, 22, No. 9, 3788–3793; 1989.

Seigou Kawaguchi et al, Infrared and Ultraviolet Spectroscopic Studies on Intramolecular Hydrogen Bonding in an Alternating Copolymer of Isobutylene and Maleic Acid, *Macromolecules*, 24, No. 22, 6030–6036; 1991.

Keling Han et al, Ionomers: The Sodium Salt of Poly(ethylene–co–Methacrylic Acid), *Journal of Applied Polymer Sciences*, vol. 38, pp. 73–86; 1989.

U. Eschenauer et al, Near–Infrared spectroscopy in chemical research, quality assurance and process control, *Introduction to NIR Spectroscopy*, pp. 12–18.

E.W. Crandall, et al, The Near Infrared Spectra of Some Polyamic Acid Resins, *Journal of Applied Polymer Science*, vol. 19, pp. 897–903; 1975.

(List continued on next page.)

*Primary Examiner*—Arlen Soderquist

[57] ABSTRACT

A process for measuring and controlling at an aim point the neutralization of an organic acid in an organic polymer solution using a near-infrared analyzer.

11 Claims, 3 Drawing Sheets

OTHER PUBLICATIONS

R.C. Moesner, Utility of near–infrared analyzers for real-time process control, *Process Control and Quality*, Elsevier Science Publishers B. V., Amsterdam, vol. 2, pp. 237–247; 1992.

U. Eschenauer, et al, Physical Properties of Synthetic High Polymers, *Chemical Abstracts*, vol. 119, No. 18, p. 26; 1993.

W.J. MacKnight et al, Properties of Ethylene–Methacrylic Acid Copolymers and Their Sodium Salts: Infrared Studies, *The Journal of Physical Chemistry*, vol. 72, No. 4, pp. 1122–1126; Apr. 1968.

E.P. Otocka et al, Properties of Ethylene–Acrylic Acid Copolymers, *Macromolecules*, vol. 1, No. 3, 244–249; May, Jun. 1968.

R. Longworth, Thermoplastic Ionic Polymers: Ionomers, *Ionic Polymers*, John Wiley & Sons, pp. 69–172, May 2, 1975.

R.E. Schirmer, Remote Optical Monitoring of Polymer Processing Over Long Fiber Optic Cables; ISA Transactions, vol. 28, No.2, pp. 65–69.

W.G. Fateley, et al, The Tenets for Using Eletromagnetic Radiation in Analytical and Structural Chemistry; CPAC Informational, Informational Document Announcement #53; pp. 1–28, Aug. 9, 1994.

S. Foulk et al. *Am. Lab.* 1987, 19, 52–53.

B. Feldhaeuser et al. *Proc. SPIE–Int. Soc. Opt. Eng.* 1989, 1145, 158–160.

M. K. Phelan et al. *Anal. Chem.* 1989, 61, 1419–1424.

Y. Wang et al. *Appl: Spectros.* 1992, 46, 764–771.

W. G. Hensen in "Near Infra–Red Spectroscopy" K.I. Hildrum, ed. Horwood; Chichester, UK, 1992, pp. 29–34.

P.B. Petersen et al. *Monogr.—Eur. Brew. Conv.* 1993, 20, 56–72.

PROCESS FOR NEUTRALIZING ACIDS IN A SOLUTION OF SOLVENT AND POLYMER

This is a continuation in part of the earlier application Ser. Nos. 08/299,379, filed Sep. 1, 1994 now abandoned.

BACKGROUND OF THE INVENTION

This invention relates to the measurement and control of the neutralization of acid, in a solution of polymer dissolved in an organic solvent, at an aim point using near-infrared spectroscopy.

It is known from the prior art that there is a correlation between the absorbance in the near-infrared and some physical or chemical property of a system. However, no methods have previously been disclosed for determining and controlling the neutralization of an inorganic acid in an organic polymer solution using near-infrared spectroscopy.

SUMMARY OF THE INVENTION

A process for measuring and controlling the neutralization of an inorganic acid in an organic polymer solution at an aim point using a near-infrared analyzer, said process comprising the steps of:

a) adding a base to a polymer solution having an inorganic acid to create a reacting solution;

b) obtaining averaged absorbance spectra of the reacting solution;

c) comparing the intensity of the absorbance spectra of the reacting solution in the range of the wavelengths from about 1300 to 1610 nanometers to that of a predictive neutrality model and computing a percent neutrality value of the reacting solution; and d) comparing the percent neutrality value to the setpoint neutrality value and adjusting the amount of base added to the acidic polymer solution.

Another embodiment of this invention is the use of the absorbance spectra of the reacting solution in the range of wavelengths from about 800–1200 nm and 1800–2200 nm in this process.

DETAILED DESCRIPTION OF THE INVENTION

Figure 1:
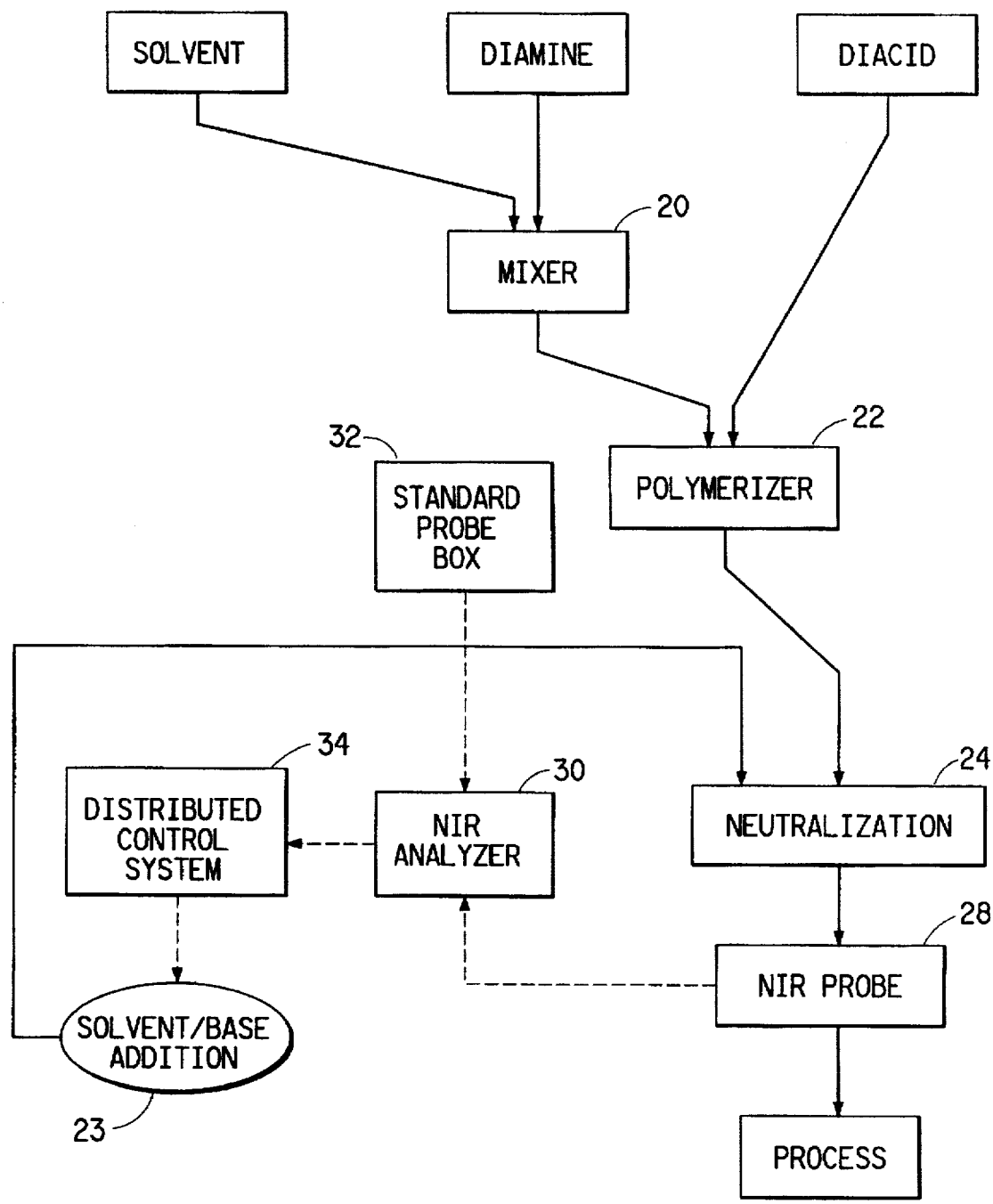
FIG. 1 is a flowsheet of a solutioning process for an aromatic polymer using a near-infrared analyzer for measuring and controlling the process.

This invention provides improved process control of the neutralization of acids in aromatic polyamide polymer solutions, particularly solutions of aramid polymers in amide solvents which contain hydrochloric acid. Aromatic polymers useful in this invention include poly (metaphenylene isophthalamide), and other aramid polymers. By "aramid" is meant a polyamide wherein at least 85% of the amide (—CONH—) linkages are attached directly to two aromatic rings. Additives can be used with the aramid and, in fact, it has been found that up to as much as 10 percent, by weight, of other polymeric material can be blended with the aramid or that copolymers can be used having as much as 10 percent of other diamine substituted for the diamine of the aramid or as much as 10 percent of other diacid chloride of the aramid. Aromatic polyamide polymers useful in this invention are disclosed in U.S. Pat No. 3,287,324 to Sweeny and U.S. Pat No. 3,063,966 to Kwolek, both of which are incorporated by reference. Solvents useful in this invention include amide solvents like dimethyl acetamide, dimethyl formamide, n-methyl pyrrolidone, and the like. Aramid polymers are made by polymerizing an aromatic diamine and an aromatic diacid in an amide solvent. After the polymerization, excess solvent is removed to achieve adequate solution viscosities to form fibers, films, and the like.

During the polymerization of aromatic polyamide polymers, byproduct acidic species can be created in the polymer solution. In a typical aramid polymerization, this acidic species is an inorganic acid, namely hydrochloric acid. In this organic system there is little or no water present initially, and the hydrochloric acid forms various acidic complexes with the solvent and the polymer. Specifically, in the case of the reaction of metaphenylene diamine and isophthaloyl chloride in dimethyl acetamide to form poly (metaphenylene isophthalamide), the dimethyl acetamide and the poly(metaphenylene isophthalamide) can form complexes with the hydrochloric acid to form various acidic resonant species. These acid species are highly reactive, and to avoid corrosion and other problems it is desired to convert these acidic species to a less reactive form, normally a salt. This is accomplished by neutralizing the hydrochloric acid which is complexed in these acidic species by the addition of a base to the polymer solution.

The base used to neutralize the acid must be a base which is at least partially soluble in the solvent. For example, calcium hydroxide, a common base, is partially soluble in dimethyl acetamide. Therefore, the preferred base addition method is to create a dispersion of the solid base in the same solvent as the polymerization solvent, and add this dispersion directly to the polymer solution having the acidic species. The addition of the base to the polymer solution initiates a reaction to neutralize the acidic species and forms water in the neutralization reaction. Solubility of the base affects the rate of the neutralization reaction, since the base is only partially soluble in the solvent, the time required to neutralize all of the acid in the solution is controlled by the time required for dissolution of the base into the solvent, which may take several hours to complete. Additionally when all the acid is neutralized, any excess base produces turgidity which does not decrease over time since the acid species is no longer present to react with and therefore solubilize the base.

This invention is useful in that NIR can be used at almost any time after the addition of the base into the acidic polymer solution to determine to what extent the acid will eventually be neutralized in the polymer solution and provide information for the control of the amount of base to be added to the polymer solution. A predictive model or equation for the solution at the point of measurement is developed by NIR scans of representative samples of the reacting polymer solution; the neutralization reaction is completed and the amount of water formed or excess base remaining is determined. Therefore, a correlation can be developed between the spectra of the solution at a point in the process and the eventual effect of the base addition to the polymer solution.

As shown in FIG. 1, a solution of a diamine, typically metaphenylene diamine, and solvent, typically dimethyl acetamide, is made by adding diamine to the solvent and mixing in a mixer 20. The solution is then mixed with a diacid chloride, typically isophthaloyl chloride, in a polymerizer 22 to form a polymer solution containing an acidic byproduct, normally hydrochloric acid. A base, normally a dispersion of additional solvent and calcium hydroxide prepared in a base/solvent addition step 23, is added to the acidic polymer solution in the neutralization step 24 to initiate the neutralization of the acidic byproduct.

To obtain good control of the addition of base, the absorbance of the reacting polymer solution after addition of the base is continuously measured and determined by a near-infrared radiation (NIR) probe 28, which outputs a process signal to a NIR analyzer 30. The NIR analyzer verifies the signal processing equipment is operating correctly by comparing the signal received by the process probe to a standard probe box 32 containing another probe and a multilayer standard. Once the accuracy of the process signal is verified, the analyzer computer processes the process signal and generates an output signal, representative of the percent neutrality of the polymer solution to a distributed control system 34. The distributed control system compares the output signal to the setpoint concentration and controls the addition of base to the process. The polymer solution can now be used in additional process steps to make fibers, films, and the like.

Figure 2:
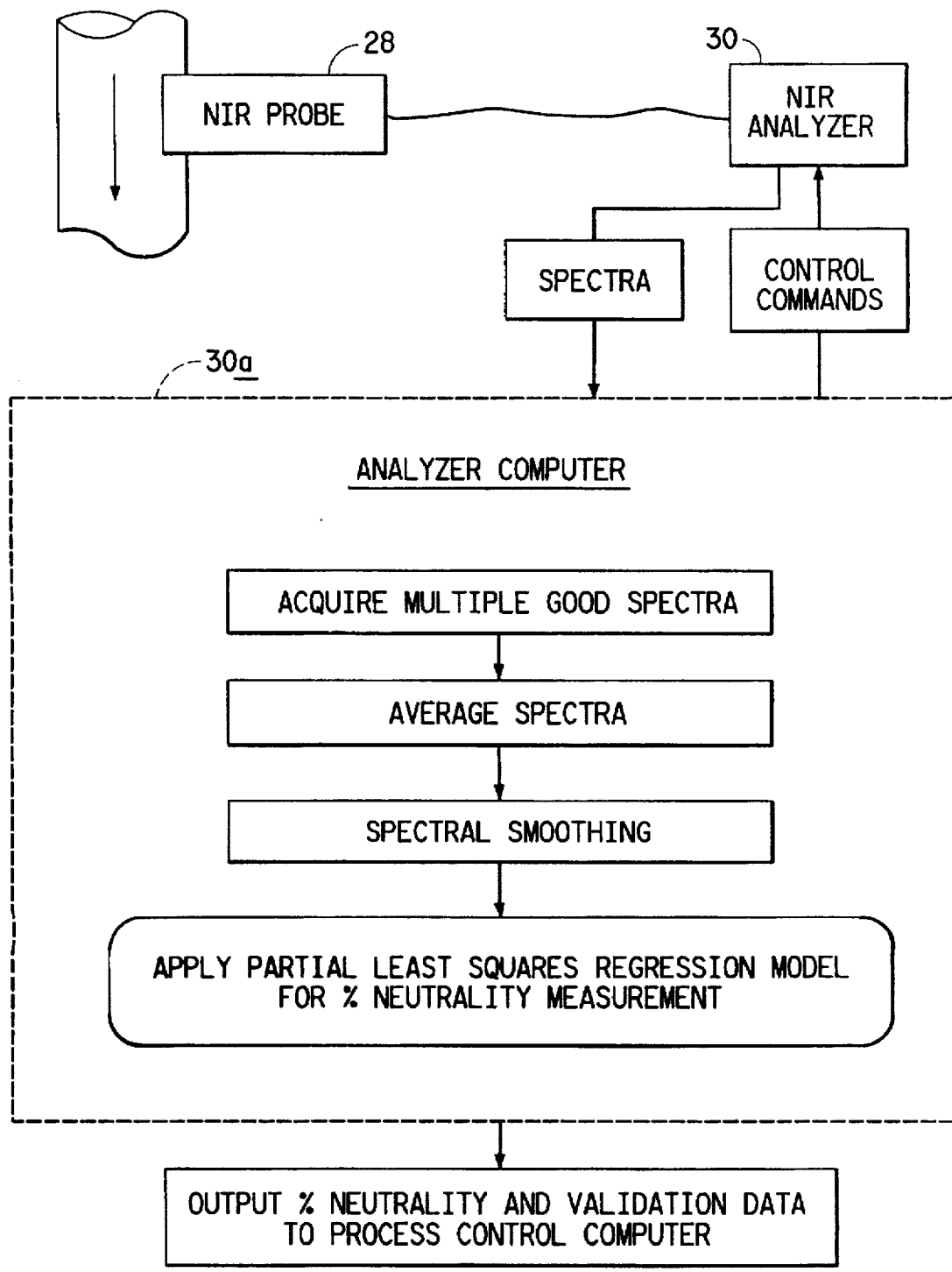
FIG. 2 represents a flowsheet of the computing steps performed in the near-infrared analyzer.

Referring now to FIG. 2, the NIR analyzer obtains a process signal from a NIR probe located on-line, and sends spectra to the analyzer computer 30a. The computer performs two functions, (1) sending control commands to the NIR analyzer, and (2) calculations on the spectra to determine percent neutrality. The calculations utilize multiple good spectra, on which they first average the measured values for the various wavelengths to generate an average spectra and smooth the spectra one or more times using multi-point spectral smoothing. The computer then applies a partial least squares regression model to the intensity of the spectra for absorbance region between 1300 and 1610 nanometers, the region representative of at least part of the chemical species which are undergoing change during the neutralization reactions in the polymer solution, to generate a value for percent neutrality, and this is outputted to the distributed control system.

100% neutrality is by definition full neutralization of the acid created during polymerization. A neutrality of 98% represents a condition wherein only 98% of the required base has been added; a neutrality of 103% represents a condition wherein 3% excess base has been added. In an organic polymer system, a "neutral" solution does not mean the solution has a "measured pH" of 7; in the case of an aramid polymer solution, the "measured pH" of a fully neutralized solution will be in the range of 5 to 6.

Figure 3:
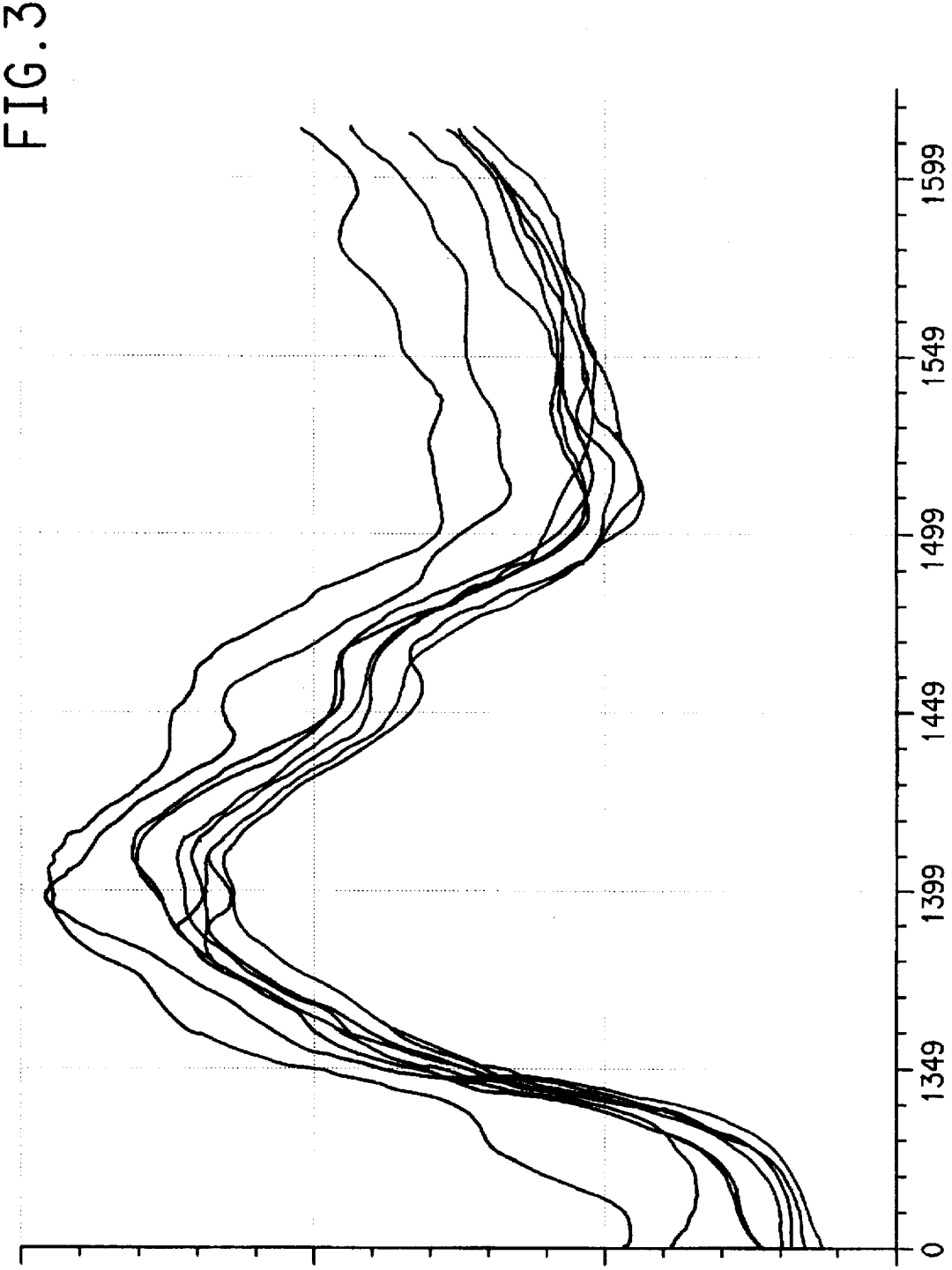
FIG. 3 shows spectral scans over the near-infrared region of 1300 to 1600 nm for polymer solutions that range in percent neutralization from 80 to 110. The x-axis shows absorbance for a 10 mm cell path, while wavelength is shown along the y-axis.

FIG. 3 shows typical near-infrared spectra for the neutralization of the acid complex formed when isophthaloyl chloride is reacted with metaphenylene diamine. The polymer solution contains not only the molecular species, but solid particles of unreacted base. Some of these particles are of the proper size to defract, refract and/or reflect the incoming near-infrared beam causing the recorded spectral absorbances to be complex and unpredictable. In addition, the wavelengths normally associated with the carbon oxygen double bond, the nitrogen hydrogen bonds and any associated hydrogen bonding of these groups, which would be expected to show absorbance variations during the neutralization reaction, remain substantially unchanged and prove useless in making meaningful correlation to the extent of the neutralization reaction. The two changes that are observed and are illustrated in FIG. 3 are the growth of the absorbance due to the formation of water and the increasing baseline due to the increasing turbidity. It is these two changes that may be followed by near-infrared and used to measure the extent of neutralization. The unpredictability of the near-infrared absorbance due to the presence of particulate in the solution and the very low concentration of water in the solution, even at the point of complete neutralization, require that an entire spectral range must be processed and averaged in order to provide an accurate and precise measure of the extent of the neutralization reaction.

It is surprising the neutralization of an acid in an organic polymer solution can be controlled by the use of near-infrared spectroscopy. Measurement and control of aqueous systems are known, but these systems either monitor the proportional growth or the shifting of peaks associated with the presence of —OH ions in the system. Since aqueous systems by definition contain a large quantity of water, the signal for use in control is very strong. In the organic system of this invention, there is essentially no water in the system until it is created when the base is added to the polymer solution, and this amount of water is of a very small amount, typically less than a total of 3% water when the acid neutralization is complete, and even less amounts in the reacting acidic polymer solution.

However, with the use of partial least squares regression chemometric techniques, the variation in these spectra can identified and modeled. Partial least squares techniques, by definition, use all the data points selected in the spectral region being analyzed. Although it is possible for a mathematician, scientist, or engineer to generate predictive equations, it is usually simpler to employ computer programs supplied by manufacturers of NIR spectroscopy equipment. The preferred procedure for generating predictive equations useful in this invention uses Partial Least Squares (PLS) Regression algorithms. These algorithms assume a predictive equation of the form:

$$N = a(0) + a(1)r(1) + a(2)r(2) + \ldots + a(n)r(n)$$

where N=predicted % neutrality of the samples;

r(1), r(2), . . . r(n)=spectral responses at wavelengths 1,2, . . . n; and a(0), a(1),a(2), . . . a(n)=constant coefficients.

The PLS algorithm begins by assuming the existence of one loading factor. Loading factors are related to the physical phenomena which contribute to the production of error between the predicted neutrality and the actual neutrality. The PLS algorithm calculates the constant coefficients of the predictive equation accounting for only one error-producing loading factor, and in turn, calculates the predicted neutrality for the samples scanned. The predicted % neutrality is then compared with the actual % neutrality. Ideally, the relationship between the predicted and actual neutralities, when the pairs are ordered numerically from the smallest to largest, is linear. Therefore, predicted and actual neutralities can be correlated by any standard statistical method, including linear least squares regression, and the quality of the correlation can be determined by numerical evaluation of one or more appropriate statistical parameters, such as, for example, the correlation coefficient and the sum of the squares of the residuals.

The remarkable fact about the regression model used in this invention is that the model can be generated from a system having very little water with only one loading factor which accounts for 96.3% of the variance in the data. It is not uncommon to need more than one loading factor to generate an acceptable model which will explain more than 90% of the variance in the data. The fact that one loading factor successfully models this system means that an adequate, well-behaved signal can be obtained from a predominantly organic system, even one having turbidity; and this signal can be used to control the neutralization of acidic species in this organic system.

Near-infrared (NIR) spectroscopy is conducted with specialized computerized equipment known as the near-infrared (NIR) spectrometer. There are several suppliers of such equipment, including UP Guided Wave, El Dorado Hills, Calif.; NIR Systems, Silver Spring, Md.; and L.T. Industries, Inc., Rockville, Md. The equipment vendors normally supply, with their equipment, a comprehensive set of operating software, which permits the user to operate his or her NIR spectrometer and to analyze the data. A computer is attached to the spectrophotometer for control of the device and interpretation of the spectral data.

When one of these spectrophotometers is used to scan a sample or process sample stream, a lengthy series of discrete results are collected at each wavelength step by the instrument. The resulting response at each wavelength can be expressed in transmittance (T), reflectance (R), or absorbance (A) units, A being equal to log (1/T). When T=1, no absorption occurs; while when T=0, infinite absorption occurs. If these results are plotted vs. wavelength, a spectrum (curve) is produced.

There are many well-known mathematical techniques of correlation of NIR spectral responses. They include, for example, "Single-Term Linear Regression," "Multiterm Linear Regression," "Component Spectrum Reconstruction," and "Discriminant Analysis" methods explained in an article by W. R. Hruschka at pp. 35–55 of Near-Infrared Technology in the Agricultural and Food Industries, P. C. Williams et al., Editors, American Association of Cereal Chemists, Inc., St. Paul, Minn., 1987 ("Williams"). Other techniques include, for example, "Hruschka Regression," "Fourier Transform Regression," "Principal Component Regression," and "Partial Least Squares Regression" methods explained in detail in an article by H. Martens et al. at pp. 57–87 of Williams. In Chapter 3 of Multivariate Calibration, H. Martens et al., John Wiley & Sons, Ltd., Chichester, U.K. 1989, more techniques, including, for example, "Univariate Calibration," "Bilinear Modeling," "Self Deconvolution," "Target Transformation Factor Analysis," "Rank Annihilation Method," "Step-Wise Multiple Linear Regression," "Ridge Regression," "Nonlinear Regression," and "Nonparametric Regression" are taught. The "Neural Network" technique explained in D. E. Rumelhart et al. in Parallel Distributed Processing-Explorations in the Micro-construction of Cognition, Vol. 1, Foundations 1986; and Vol. 2, Psychological and Biological Models, 1986; and Vol. 3, A Handbook of Models. Programs and Exercises, 1988, MIT Press Cambridge, Mass., may also be applied.

Some commercially available software packages include, for example, "Near-Infrared Spectral Analysis Software" (NSAS) by NIR Systems, Inc., Silver Spring, Md.; "Unscrambler" by Camo A/S, Trondheim, Norway; "Spectra Metrix," "LightCal," and "LightCal Plus" by L. T. Industries Corporation, Rockville, Md.; and "InfraAnalyzer Data Analysis System" (IDAS) and "Principal Component Analysis Program" (PCA-pc) by Bran+Luebbe Analyzing Technologies, Inc.

In general, the extent of the neutralization of the acid in an aramid polymer solution process streams can be predicted by the application of near-infrared spectroscopy, within the wavelength range of 800–2200 nm, especially 1300–1610 nm. The method requires establishing a correlation between the % neutrality of samples of a training set and their near infrared spectra, developing from that correlation a predictive equation, verifying the accuracy of the predictive equation on samples of a validation set, and applying the predictive equation to the determination of the composition of unknown samples. It has also been found that the measurement task can also be undertaken at other wavelengths, including 800–1200 nm and 1800–2200 nm.

The absorbance may be measured as the absorbance, or as the first, second, third, fourth or higher derivative of absorbance or by other signal processing techniques. Multiple scans are made (2 or more) using in-line fiber-optic near-infrared probes operating in transmission. The transmittance or absorbance at each wavelength within the ranges of interest is stored for each nanometer wavelength separation in order to create each spectrum. The spectra are then averaged. The averaged spectrum is then subjected to one or more spectral smoothing operations to further reduce noise in the spectral data. The spectrum is then stored together with analytical data in order to prepare a training set of known data for regression analysis. The training set is then subjected to various regression analysis methodologies in order to discover the most robust mathematical expression in the form of a predictive equation for calculating the desired measurement from the spectral responses.

The predictive mathematical expression generated during the training process described above is then routinely applied to the in-line measurement of the same species in the process stream. The routine analyses are undertaken at process conditions which are within the envelope of conditions used during the training process. The routine spectra are subjected to the identical data treatments utilized with the training set spectra.

Near-infrared spectrometers and modified IR spectrometers of conventional design may be used with the invention. Preferred modes of operation are transmission, reflectance, and transflectance. Suitable spectrometers are the NIR Systems model 6500; LT Industries model 1200; and the Guided Wave model 300 series. The spectrometer can be operated on a batch basis (receiving signals, e.g. by a sample feeding arrangement), or, more preferably, on a continuous basis in which the fluid to be measured flows through a cell, or a probe immersed in the flowing fluid transmits optically through a fiber-optic cable to the spectrophotometer. The technique for sampling, measuring, and signal processing can be conventional and is well-known to those skilled in the art.

In the preferred practice of this invention, a spectrum is produced having wavelengths in nanometers along the x-axis and magnitude of absorbance along the y-axis. Three measurements of the magnitude of the absorbance for each wavelength are averaged to generate one spectrum composed of the averaged magnitude of the absorbance for each wavelength. The spectrum is smoothed twice utilizing a Savitsky-Golay smoothing algorithm employing 17 spectral data points (center wavelength and 8 nm on either side). This is done to improve the signal-to-noise ratio, and is just one technique known by persons skilled in the art. The studies of Savitsky and Golay are among the early developments of least-squares polynomial smoothing in analytical chemistry. They have demonstrated that the noise in every window is reduced by a factor approximately equal to the square root of the span of the window, provided the noise is normally distributed. Note, however, that the larger the window the higher the loss of resolution. They have also tabulated the coefficients needed for the smoothing formulas using various models (e.g., quadratic and higher-order polynomials and their derivatives) and various window spans. (A. Savitsky and M. J. E. Golay, "Smoothing and Differentiation of data by Simplified Least Squares Procedures," Anal. Chem. 36, 1627 1964).

Based on the information obtained by the spectral analysis, the % neutrality of the polymer solution can then be automatically adjusted in any appropriate means, but normally this is accomplished by the addition of more or less base/solvent mixture to the polymer solution. After the neutralization is complete, the polymer solution can then be used for the production of shaped articles like fibers, films, fibrids, and the like.

What is claimed is:

1. A process for measuring and controlling the neutralization of an inorganic acid in an organic polymer solution at an aim point using a near-infrared analyzer and growth of absorbance due to the formation of water and increasing turbidity, said process comprising the steps of:
   a) adding a base to a polymer solution having an inorganic acid to create a reacting solution;
   b) obtaining multiple spectra;
   c) averaging the measured values for the various wavelengths to generate an average spectra;
   d) smoothing the averaged spectra one or more times using multi-point spectral smoothing;
   e) applying a partial least squares regression model to the intensity of the spectra of the reacting solution for the absorbance region from about 1300 to 1610 nanometers to generate a a value for percent neutrality; and
   f) comparing the percent neutrality value to the setpoint neutrality value and adjusting the amount of the base and solvent mixture added to the acidic polymer solution.

2. The process of claim 1 wherein the organic polymer solution is an aromatic polymer solution of an aromatic polymer in an organic solvent.

3. The process of claim 2 wherein the aromatic polyamide polymer is an aramid polymer.

4. The process of claim 2 wherein the aromatic polyamide polymer is poly(meta-phenylene isophthalamide).

5. The process of claim 1 wherein the organic solvent is diethyl acetamide.

6. A process for measuring and controlling the neutralization of an inorganic acid in an organic polymer solution at an aim point using a near-infrared analyzer and growth of absorbance due to the formation of water and increasing turbidity, said process comprising the steps of:
   a) adding a base to a polymer solution having an inorganic acid to create a reacting solution;
   b) obtaining multiple spectra;
   c) averaging the measured values for the various wavelengths to generate an average spectra;
   d) smoothing the averaged spectra one or more times using multi-point spectral smoothing;
   e) applying a partial least squares regression model to the intensity of the spectra of the reacting solution for the absorbance region from about 800 to 1200 nanometers to generate a a value for percent neutrality; and
   f) comparing the percent neutrality value to the setpoint neutrality value and adjusting the amount of the base and solvent mixture added to the acidic polymer solution.

7. The process of claim 6 wherein the organic polymer solution is an aromatic polymer solution of an aromatic polymer in an organic solvent.

8. The process of claim 7 wherein the aromatic polyamide polymer is poly(meta-phenylene isophthalamide) and the organic solvent is dimethyl acetamide.

9. A process for measuring and controlling the neutralization of an inorganic acid in an organic polymer solution at an aim point using a near-infrared analyzer and growth of absorbance due to the formation of water and increasing turbidity, said process comprising the steps of:
   a) adding a base to a polymer solution having an inorganic acid to create a reacting solution;
   b) obtaining multiple spectra;
   c) averaging the measured values for the various wavelengths to generate an average spectra;
   d) smoothing the averaged spectra one or more times using multi-point spectral smoothing;
   e) applying a partial least squares regression model to the intensity of the spectra of the reacting solution for the absorbance region from about 1800 to 2200 nanometers to generate a a value for percent neutrality; and
   f) comparing the percent neutrality value to the setpoint neutrality value and adjusting the amount of the base and solvent mixture added to the acidic polymer solution.

10. The process of claim 9 wherein the organic polymer solution is an aromatic polymer solution of an aromatic polymer in an organic solvent.

11. The process of claim 10 wherein the aromatic polyamide polymer is poly(meta-phenylene isophthalamide) and the organic solvent is dimethyl acetamide.

* * * * *